United States Patent [19]

Sawayanagi

[11] Patent Number: 5,602,234
[45] Date of Patent: Feb. 11, 1997

[54] STABLE ANTIBODY SOLUTION AND METHOD FOR PREPARING SAME

[75] Inventor: Yoichi Sawayanagi, Tokyo, Japan

[73] Assignee: Dojin Iyaku-Kako Co., Ltd., Tokyo, Japan

[21] Appl. No.: 387,375

[22] Filed: Feb. 13, 1995

Related U.S. Application Data

[63] Continuation of Ser. No. 167,198, Dec. 16, 1993, abandoned.

[30] Foreign Application Priority Data

Dec. 17, 1992 [JP] Japan ................................ 4-337478

[51] Int. Cl.$^6$ ........................ C07K 16/00; C07K 14/765
[52] U.S. Cl. ................... 530/390.5; 530/363; 530/387.1; 530/391.1; 530/362
[58] Field of Search ........................... 530/391.1, 387.1, 530/362, 390.5, 363

[56] References Cited

U.S. PATENT DOCUMENTS

| 4,474,893 | 10/1984 | Reading ................................ 436/547 |
| 4,650,772 | 3/1987 | Dodge et al. ........................ 436/548 |
| 4,722,899 | 2/1988 | Hamaoka et al. .................... 435/172.2 |
| 4,748,018 | 5/1988 | Stolle et al. .......................... 424/92 |

FOREIGN PATENT DOCUMENTS

| 0170983 | 2/1986 | European Pat. Off. . |
| 0539584 | 5/1993 | European Pat. Off. . |
| 57-145818 | 9/1982 | Japan . |
| 62-289523 | 12/1987 | Japan . |
| 4173799 | 6/1992 | Japan . |
| 1180957 | 2/1970 | United Kingdom . |
| 9201808 | 2/1992 | WIPO . |

OTHER PUBLICATIONS

Japanese Journal of Mycoplasmology, Proceedings of the XX annual Congrass of the Japanese Society of Mycoplasmology, pp. 65–70 (May 29, 1993).
Seki et al., Jpn. J. Vet. Sci. vol. 50(2), pp. 383–393 (1988).
MacDonald et al., J. Med. Microbiol. vol. 13, pp. 423–435 (1980).
Sigma catalog, pp. 336–338 (1989).
Borrebaeck, Journal of Immunological Methods, vol. 123, pp. 157–165 (1989).
Rybarska et al., Archivum Immunologiae Et Therpiae Experimentalis, vol. 39 (3), pp. 317–327 (1991).
Harlow et al, Antibodies: A Laboratory Manual, Cold Springs Harbor Laboratory, New York, 1988, pp. 287, 289–299.
J. Dent. Res., 1976, 55: pp. A33–37, Hebert et al.

*Primary Examiner*—Frank C. Eisenschenk
*Attorney, Agent, or Firm*—Sughrue, Mion, Zinn, Macpeak & Seas

[57] ABSTRACT

An antibody solution containing (1) an antibody or a labelled antibody, (2) albumin, and (3) an azo dye containing naphthalenesulfonic acid in its structure and a method for stabilizing an antibody or a labelled antibody comprising adding albumin and an azo dye containing naphthalenesulfonic acid in its structure to a solution of an antibody or a labelled antibody are disclosed.

2 Claims, No Drawings

STABLE ANTIBODY SOLUTION AND METHOD FOR PREPARING SAME

This is a Continuation of application Ser. No. 08/167,198 filed 16 Dec. 1993, now abandoned.

FIELD OF THE INVENTION

This invention relates to a stable antibody or labelled antibody solution and to a method for stabilizing an antibody or a labelled antibody.

BACKGROUND OF THE INVENTION

A number of diagnostic reagents using an antibody or a labelled antibody have recently been developed. In particular, a monoclonal antibody has been steadily extending its utility in the field of diagnosis and therapeutic drugs because of its high reaction specificity.

Many of antibodies, especially monoclonal antibodies composed of a single protein, have a unique character, which has made it difficult to obtain a stable solution thereof. Similarly to general enzyme proteins, methods of preserving antibodies include freezing, lyophilization and ammonium sulfate fractionation followed by suspension. However, these methods not only involve complicated steps not easy to carry out but require much labor for preparing an antibody solution from the preserved state on use.

Studies have thus been given to a method for preserving an antibody in the form of a solution. Proposals so far made for obtaining an antibody solution include a method of adding albumin (WO 92/01808 corresponding to EP-A-0 539 584) and a method of adding hydrolyzed egg albumin (JP-A-61-76423 corresponding to U.S. Pat. No. 4,650,772 and EP-A-0 170 983, the term "JP-A" as used herein means an "unexamined published Japanese patent application"). These methods, however, are still unsatisfactory for preparing a stabilized antibody solution.

SUMMARY OF THE INVENTION

An object of the present invention is to provide a stable antibody solution.

Another object of the present invention is to provide a method for stabilizing an antibody.

As a result of extensive investigations, the present inventors have found that addition of a specific azo dye which has no stabilizing effect when used alone to an antibody solution containing albumin surprisingly brings about a marked improvement in antibody stability. The present invention has been completed based on this finding.

The present invention provides an antibody solution containing (1) an antibody or a labelled antibody, (2) albumin, and (3) an azo dye containing naphthalenesulfonic acid in its structure.

The present invention also provides a method for stabilizing an antibody or a labelled antibody comprising adding albumin and an azo dye containing naphthalenesulfonic acid in its structure to a solution of an antibody or a labelled antibody.

DETAILED DESCRIPTION OF THE INVENTION

The antibody which can be stabilized according to the present invention is not particularly limited in kind and concentration, etc., and may be selected appropriately depending on the use. If desired, the antibody selected may be labelled with, for example, fluorescent substance, such as fluorescein or rhodamine; biotin; enzyme, such as peroxidase or alkaline phosphatase; radioactive substance, such as $^{125}I$ and the like.

The concentration of the antibody in the antibody solution of the present invention varies depending on the type of the antibody. For example, anti-Mycoplasma pneumonia monoclonal antibody G1-E6 is contained in a concentration ranging from 10 to 200 μg/ml.

Albumin which can be used in the present invention includes bovine serum albumin, human albumin, ovalbumin, lactalbumin, etc. Since monoclonal antibodies are composed of a single protein unlike a polyclonal antibody obtained from antiserum, they mostly have a specific character and their stability varies depending on the kind. Accordingly, where the antibody to be stabilized is a monoclonal antibody, it is desirable to select one or more kinds of albumin species according to the kind of the antibody. The albumin is used in an amount effective to stabilize the antibody, preferably in a concentration ranging from 1 to 20 mg/ml in the antibody solution, though varying depending on the kind of the antibody.

The azo dye containing naphthalenesulfonic acid in its structure includes, for example, Direct Green 1, Direct Green 6, Direct Green 59, Direct Black 4, Direct Black 22, Direct Black 38, Direct Blue 1, Direct Blue 6, Direct Blue 53 (Evan's Blue), Direct Red 2, Direct Red 28 (Congo Red), and Direct Red 79, etc.

Although these azo dyes make no contribution to stabilization of an antibody when used alone, they exhibit a high stabilizing activity when combined with albumin. While varying depending on the kind of the antibody used, the azo dye is added in an amount effective to enhance antibody-stabilizing ability of albumin, preferably in a concentration ranging from 1 to 100 μg/ml in the antibody solution. Usually, one kind of azo dyes would be sufficient. If necessary, two or more kinds of azo dyes may be used at an appropriate ratio.

A buffer solution having a neutral pH value can be used as a solution to which the components are added. Examples of the buffer solutions include physiological saline, phosphate buffer, Tris-hydrochloride buffer, HEPES buffer and the like. The pH value of the antibody solution is adjusted to 5 to 9, preferably 6 to 8, though it varies depending on the type of the antibody.

If desired, the antibody solution according to the present invention may further contain antiseptics or preservatives, such as sodium azide and the like.

The antibody solution of the present invention can be prepared by mixing the above-mentioned essential components (1) to (3) in a usual manner. For example, an antibody is dissolved in a solution containing 1 to 20 mg/ml of albumin, and an azo dye is then added thereto in a concentration of from 1 to 100 μg/ml. It is also possible to mix an antibody solution with a separately prepared solution containing the other components. The order of addition of components (1) to (3) is not restricted. Thereafter, if desired, an antiseptic, a preservative or any other additives may be added and dissolved oxygen may be removed from the solution. The resulting solution may be then put into a light-shielding container to provide a final product of a stable antibody solution.

The antibody solution of the present invention can be used as a diagnosing reagent, a reagent for detecting various antigens and the like.

According to the present invention, an antibody can be preserved stably in the form of a solution which is convenient for use.

The present invention will now be illustrated in greater detail with reference to Examples and Test Examples, but the present invention should not be construed as being limited thereto. Monoclonal antibodies used in Examples are as follows.

Antibody Cel-E6 is disclosed in JP-A-63-184064.

Antibodies C2H5-C10 and 3-19-11 each were prepared by the same method as disclosed in JP-A-63-184064.

An IgG mAb to *Candida albicans* protease was made as follows. A mouse (Balb/c, female) was immunized with acidic protease of a pathogenic yeast, *Candida albicans* (see F. Macdonald and F. C. Odds, *J. Med. Microbiol.*, Vol. 13, pp. 423–435 (1980)) together with complete Freund's adjuvant. After a booster shot, spleen cells of the animal and myeloma cells (X63-Ag8.6.5.3) were fused together with the aid of polyethylene glycol according to the process described in JP-A-63-184064. The resulting monoclonal antibody-producing hybridoma was cultured to recover the produced monoclonal antibody.

EXAMPLE 1

Eight milliliters of a 1 mg/ml solution of FITC (fluorescein isothiocyanate)-labelled anti-Mycoplasma pneumonia monoclonal antibody (G1-E6) in a 50 mM phosphate buffer (pH 7.0) were mixed with 92 ml of a 50 mM phosphate buffer (pH 7.0) containing 500 mg of bovine serum albumin (BSA), 850 mg of sodium chloride, 4 mg of Evan's Blue, and 50 mg of sodium azide to prepare 100 ml of an antibody solution. The solution was put in brown glass bottles in an amount of 1 ml per bottle.

COMPARATIVE EXAMPLE 1

An antibody solution was prepared in the same manner as in Example 1, except for using no azo dye. The solution was put in brown glass bottles in an amount of 1 ml per bottle.

TEST EXAMPLE 1

Monoclonal antibody activity of a Mycoplasma pneumonia diagnostic reagent comprising the FITC-labelled monoclonal antibody prepared in Example 1 or Comparative Example 1 was determined with time by enzyme-linked immunosorbent assay (ELISA) in the following manner.

Mycoplasma pneumonia cells were immobilized on a 96-well microplate (Nunc) by physical adsorption followed by blocking with BSA. The test antibody solution was distributed to each well and incubated at 37° C. for 1 hour. After washing the wells, horseradish peroxidase-labeled anti-mouse IgG or IgM antibody solution was added to each well and incubated at 37° C. for 30 minutes. After washing the wells, an o-phenylenediamine solution was added to each well to effect color development, the reaction was terminated by adding sulfuric acid and the absorbance of the reaction mixture was measured. The antibody concentration was determined from the calibration curve which had been separately prepared. The relative activity of the antibody was calculated taking the initial activity as a standard (100).

The results obtained are shown in Table 1 below.

TABLE 1

| Preservation Time | Preservation Conditions | Relative Activity | |
|---|---|---|---|
| | | Example 1 | Comparative Example 1 |
| initial stage | — | 100 | 100 |
| 3 months | in refrigerator* | 100 | 100 |
| | at room temperature** | 90 | 70 |
| 6 months | in refrigerator* | 90 | 90 |
| | at room temperature** | 75 | 25 |

Note:
*4 to 8° C.
**20 to 25° C.

EXAMPLE 2

The following 4 antibody solutions were prepared, and the effect of stabilizing a monoclonal antibody under severe conditions was examined.

Solution A: A 0.1 mg/ml solution of an anti-Mycoplasma pneumonia monoclonal antibody (C2H5-C10, IgG) in physiological saline buffered with a 1/15 M phosphoric acid (pH 7.2).
Solution B: Solution A having further dissolved therein BSA to a concentration of 5 mg/ml.
Solution C: Solution B having further dissolved therein Congo Red to a concentration of 0.004 mg/ml.
Solution D: Solution B having further dissolved therein Congo Red to a concentration of 0.04 mg/ml.

Each of solutions A to D was sealed into a brown glass bottle and allowed to stand at 50° C. for 7 days. The residual antibody activity was measured by ELISA in the same manner as in Test Example 1. The results obtained are shown in Table 2 below.

TABLE 2

| Solution | Residual Activity (%) |
|---|---|
| A | 68 |
| B | 71 |
| C | 80 |
| D | 96 |

EXAMPLE 3

The following 4 solutions were prepared, and the effect of stabilizing a monoclonal antibody under severe conditions was examined.

Solution A: A 0.1 mg/ml solution of an anti-Mycoplasma pneumonia monoclonal antibody (3-19-11, IgM) in physiological saline buffered with a 1/15 M phosphoric acid (pH 7.2).
Solution B: Solution A having further dissolved therein BSA to a concentration of 5 mg/ml.
Solution C: Solution B having further dissolved therein Evan's Blue to a concentration of 0.004 mg/ml.
Solution D: Solution B having further dissolved therein Evan's Blue to a concentration of 0.04 mg/ml.

Each of solutions A to D was sealed into a brown glass bottle and allowed to Stand at 50° C. for 7 days. The residual antibody activity was measured by ELISA in the same manner as in Test Example 1. The results obtained are shown in Table 3 below.

TABLE 3

| Solution | Residual Activity (%) |
|---|---|
| A | 65 |
| B | 94 |
| C | 97 |
| D | 99 |

EXAMPLE 4

The following 4 solutions were prepared, and the effect of stabilizing a monoclonal antibody under severe conditions was examined.

Solution A: A 0.1 mg/ml solution of an anti-*Candida albicans* protease monoclonal antibody (IgG) described above in physiological saline buffered with a 1/15 M phosphoric acid (pH 7.2).

Solution B: Solution A having further dissolved therein BSA to a concentration of 5 mg/ml.

Solution C: Solution B having further dissolved therein Evan's Blue to a concentration of 0.004 mg/ml.

Solution D: Solution B having further dissolved therein Evan's Blue to a concentration of 0.04 mg/ml.

Each of solutions A to D was sealed into a brown glass bottle and allowed to stand at 50° C. for 3 days. The residual antibody activity was measured by ELISA in the same manner as in Test Example 1. The results obtained are shown in Table 4 below.

TABLE 4

| Solution | Residual Activity (%) |
|---|---|
| A | 52 |
| B | 66 |
| C | 71 |
| D | 76 |

While the invention has been described in detail and with reference to specific examples thereof, it will be apparent to one skilled in the art that various changes and modifications can be made therein without departing from the spirit and scope thereof.

What is claimed is:

1. A method for stabilizing an antibody or a labelled antibody comprising adding albumin and an azo dye selected from the group consisting of Direct Blue 53 (Evan's Blue) and Direct Red 28 (Congo Red) to a solution of an antibody or a labelled antibody.

2. The method as claimed in claim 1, wherein said antibody or a labelled antibody is a monoclonal antibody or a labelled monoclonal antibody.

* * * * *